US010321849B2

(12) United States Patent
Euliano et al.

(10) Patent No.: US 10,321,849 B2
(45) Date of Patent: Jun. 18, 2019

(54) SYSTEM FOR INGESTION EVENT MONITORING AND METHOD FOR DETECTING INGESTION EVENTS WITH HIGH ACCURACY

(71) Applicant: etectRx, Inc., Gainesville, FL (US)

(72) Inventors: Neil R. Euliano, Gainesville, FL (US); Brent Myers, Palm Bay, FL (US); Glen Flores, Gainesville, FL (US)

(73) Assignee: etectRx, Inc., Gainesville, FL (US)

( * ) Notice: Subject to any disclaimer, the term of this patent is extended or adjusted under 35 U.S.C. 154(b) by 0 days.

(21) Appl. No.: 15/783,801

(22) Filed: Oct. 13, 2017

(65) Prior Publication Data

US 2018/0103871 A1 Apr. 19, 2018

Related U.S. Application Data

(60) Provisional application No. 62/407,913, filed on Oct. 13, 2016.

(51) Int. Cl.
*A61B 5/00* (2006.01)
*A61B 5/07* (2006.01)

(52) U.S. Cl.
CPC ............ *A61B 5/073* (2013.01); *A61B 5/4833* (2013.01); *A61B 2560/0214* (2013.01); *A61B 2562/162* (2013.01)

(58) Field of Classification Search
CPC ........ H04B 5/0075; H04B 1/16; A61B 5/073; A61B 5/4848; A61B 5/7282; H01Q 1/27; H01Q 7/00; H03K 3/02
See application file for complete search history.

(56) References Cited

U.S. PATENT DOCUMENTS

| | | | | |
|---|---|---|---|---|
| 9,659,423 | B2* | 5/2017 | Robertson | G07C 9/00158 |
| 9,756,874 | B2* | 9/2017 | Arne | A23L 33/10 |
| 2008/0306360 | A1* | 12/2008 | Robertson | A61B 1/00016 600/302 |
| 2009/0082645 | A1* | 3/2009 | Hafezi | A61B 5/073 600/302 |
| 2009/0256702 | A1* | 10/2009 | Robertson | A61B 5/073 340/539.12 |
| 2010/0022836 | A1* | 1/2010 | Colliou | A61B 5/0031 600/118 |
| 2010/0185055 | A1* | 7/2010 | Robertson | A61B 5/0031 600/117 |
| 2011/0054265 | A1* | 3/2011 | Hafezi | A61B 5/0031 600/300 |
| 2011/0257491 | A1* | 10/2011 | Robertson | A61B 5/0031 600/302 |
| 2012/0004527 | A1* | 1/2012 | Thompson | A61B 5/0028 600/377 |
| 2012/0011699 | A1* | 1/2012 | Hafezi | A61B 5/0031 29/458 |
| 2012/0062379 | A1* | 3/2012 | Hafezi | A61B 5/073 340/539.12 |

(Continued)

*Primary Examiner* — Hoi C Lau
(74) *Attorney, Agent, or Firm* — Bass, Berry & Sims PLC (57) ABSTRACT

System and method for ingestion event detection and monitoring are disclosed. The system comprises: an ingestible microsensor configured to generate a signal representing an ingestion event upon ingestion and contact with stomach fluid of a patient; and a reader device positioned external to the patient and configured to detect the signal representing the ingestion event with at least 95% accuracy.

9 Claims, 4 Drawing Sheets

ID-Cap System Operation (56) References Cited

U.S. PATENT DOCUMENTS

| | | | | |
|---|---|---|---|---|
| 2013/0117696 A1* | 5/2013 | Robertson | ........... | G06F 19/3418 715/763 |
| 2014/0009262 A1* | 1/2014 | Robertson | ........... | A61B 5/0006 340/5.52 |
| 2014/0203950 A1* | 7/2014 | Zdeblick | ............ | G06F 19/3418 340/870.07 |
| 2015/0127737 A1* | 5/2015 | Thompson | .......... | G06F 19/3418 709/204 |
| 2015/0127738 A1* | 5/2015 | Thompson | .............. | H04W 4/80 709/204 |
| 2015/0149375 A1* | 5/2015 | Thompson | ......... | G06Q 30/0279 705/319 |
| 2015/0283036 A1* | 10/2015 | Aggarwal | ................. | A61J 7/04 206/534 |
| 2016/0029998 A1* | 2/2016 | Brister | ................ | A61B 5/6853 600/424 |
| 2016/0033667 A1* | 2/2016 | Schmidt | ................. | G01V 3/104 324/234 |
| 2016/0380708 A1* | 12/2016 | Dua | .................... | H04B 13/005 375/219 |
| 2017/0000180 A1* | 1/2017 | Arne | ....................... | A23L 33/10 |
| 2017/0270779 A1* | 9/2017 | Zdeblick | ............. | G06F 19/3418 |
| 2018/0026680 A1* | 1/2018 | Shirvani | .............. | H04B 5/0075 |
| 2018/0096547 A1* | 4/2018 | Robertson | ........... | A61B 5/0028 |
| 2018/0103871 A1* | 4/2018 | Euliano | ................. | A61B 5/073 |
| 2018/0110441 A1* | 4/2018 | Frank | ....................... | A61B 5/07 |

* cited by examiner

SYSTEM FOR INGESTION EVENT MONITORING AND METHOD FOR DETECTING INGESTION EVENTS WITH HIGH ACCURACY

CROSS-REFERENCE TO RELATED APPLICATIONS

This application claims the benefit of U.S. Provisional Patent Application No. 62/407,913, filed Oct. 13, 2016.

STATEMENT OF FEDERALLY FUNDED RESEARCH

This invention was made with government support under contract 4R44DA036277-02 awarded by the National Institute on Drug Abuse (NIDA) of the National Institutes of Health. The government has certain rights in the invention.

TECHNICAL FIELD OF THE INVENTION

The present invention relates in general to the fields of ingestion event monitoring, patient compliance with pharmaceutical prescriptions and clinical trial protocols, and reporting of medication adherence data.

SUMMARY OF THE INVENTION

The present invention is directed to a system for monitoring ingestion events and methods of detecting ingestion events with high accuracy. The system is a novel technology that provides an objective measure of medication ingestion and enables real-time reporting of verified medication adherence data. The system includes an ingestible microsensor that is embedded in an oral dosage form and, once activated by stomach fluid, communicates digital messages to an external wearable reader to confirm ingestion. The detection rate of the system for detecting ingestion events is preferably at least 95%, more preferably at least 97%, further preferably 99% and most preferably 100%.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

DETAILED DESCRIPTION OF THE INVENTION

The present invention is directed to a system for monitoring ingestion events and methods of detecting ingestion events with high accuracy. The system is a novel technology that provides an objective measure of medication ingestion and enables real-time reporting of verified medication adherence data. The system includes an ingestible microsensor that is embedded in an oral dosage form and, once activated by stomach fluid, communicates digital messages to an external wearable reader to confirm ingestion. The accuracy of the system for detecting ingestion events is preferably at least 95%, more preferably at least 97%, further preferably 99% and most preferably 100%.

The inventive system is also referred to herein as "the ID-Cap System."

Nonadherence to prescribed medications is an important consideration in the clinical management of patients and in clinical research and drug development. Considerable research has been conducted to elucidate the reasons for nonadherence, which are often unique to the individual patient and the specific medication of interest. [1] Across different disease states and medications, nonadherence directly impacts drug exposure and therapeutic outcomes. An estimated 50% of patients in developed countries are not adherent to prescribed medications for chronic health conditions, and the magnitude and impact of the problem are even greater in developing countries. [2] Poor adherence is associated with increased healthcare costs and contributes over $100 billion in avoidable medical costs in just the United States alone. [3] The accurate detection and reporting of medication nonadherence are critical for healthcare providers, payers, and clinical researchers to evaluate and optimize therapeutic interventions. Current methods that are commonly used for monitoring medication adherence, such as patient self-reports, pill counts, and prescription refill histories, comprise indirect measures that are generally incomplete and inaccurate and cannot be effectively utilized for understanding and tracking actual medication use. [4] Reliable methods for objectively measuring medication adherence behaviors that can be easily implemented for remote health monitoring are needed.

The ID-Cap System is a novel technology that provides an objective measure of medication ingestion and enables real-time reporting of verified medication adherence data at the dose level. The system is classified as an ingestible event monitoring system and used for detecting the presence of an ingested solid oral dosage form inside the gastrointestinal (GI) tract. Ingestible medical devices have been well-characterized in the scientific literature and regulatory approval processes. The ID-Cap System consists of an ingestible microsensor that is embedded in an oral dosage form and, once activated by stomach fluid, communicates digital messages to an external wearable reader to confirm ingestion. The adherence data, including time-stamped messages verifying ingestion, are transmitted to a secure, centralized database via the mobile phone network. The collection and real-time reporting of accurate medication adherence data has the potential to strengthen health information datasets and significantly improve medication use and therapeutic outcomes.

A study was conducted to evaluate the accuracy of the system for detecting ingestion events. The study design included the following three phases: 1) screening phase, 2) treatment phase consisting of 20 daily capsule ingestion events over a four-week period, and 3) follow-up phase consisting of a follow-up study visit that included an abdominal X-ray and a follow-up phone call. The initial use of the ID-Cap reader and ingestion of the first study capsule were directly observed by an investigator during the first study visit. Subsequent study capsule ingestions were completed outside the research facility at the study participant's home or other location of their choice with ingestion assessed using the ID-Cap System.

Twenty (20) healthy volunteers were enrolled in this four-week pilot study. Study measurements included ID-Tag detection indicating capsule ingestion, utilization of the ID-Cap System consistent with instructions for use, adverse event reports, discontinuations of the System during the study, and safety assessments related to excretion of the ID-Tags through abdominal X-ray evaluations.

Positive detection accuracy was 100% for the 20 directly-observed ingestions of study capsules that occurred during the initial study visits. Of the 384 ingestion events that were self-administered by the study participants without direct observation, 371 were accurately detected using the ID-Cap System. Overall adherence to the prescribed study capsules as measured by the ID-Cap System was 97.75% (391 detections/400 expected ingestion events). Significant intra-individual and inter-individual variability in the timing of self-administered doses was observed in this study. No adverse events were reported, and no study participants discontinued use of the ID-Cap System for any reason during the study. There was no evidence indicating retention of ID-Tags based on abdominal X-ray evaluations.

The ID-Cap System enables accurate measurement of medication adherence for oral drug therapy at the dose level. This study supports the clinical validation of the technology and feasibility in using the system for the collection and real-time reporting of medication adherence in the clinical management of patients and in clinical research and drug development.

The objective of this exploratory study was to evaluate the performance, reliability, usability, and safety of the ID-Cap System for remote monitoring of 20 ingestion events over four weeks in 20 healthy volunteers.

Methods

Study Participants

Figure 1:
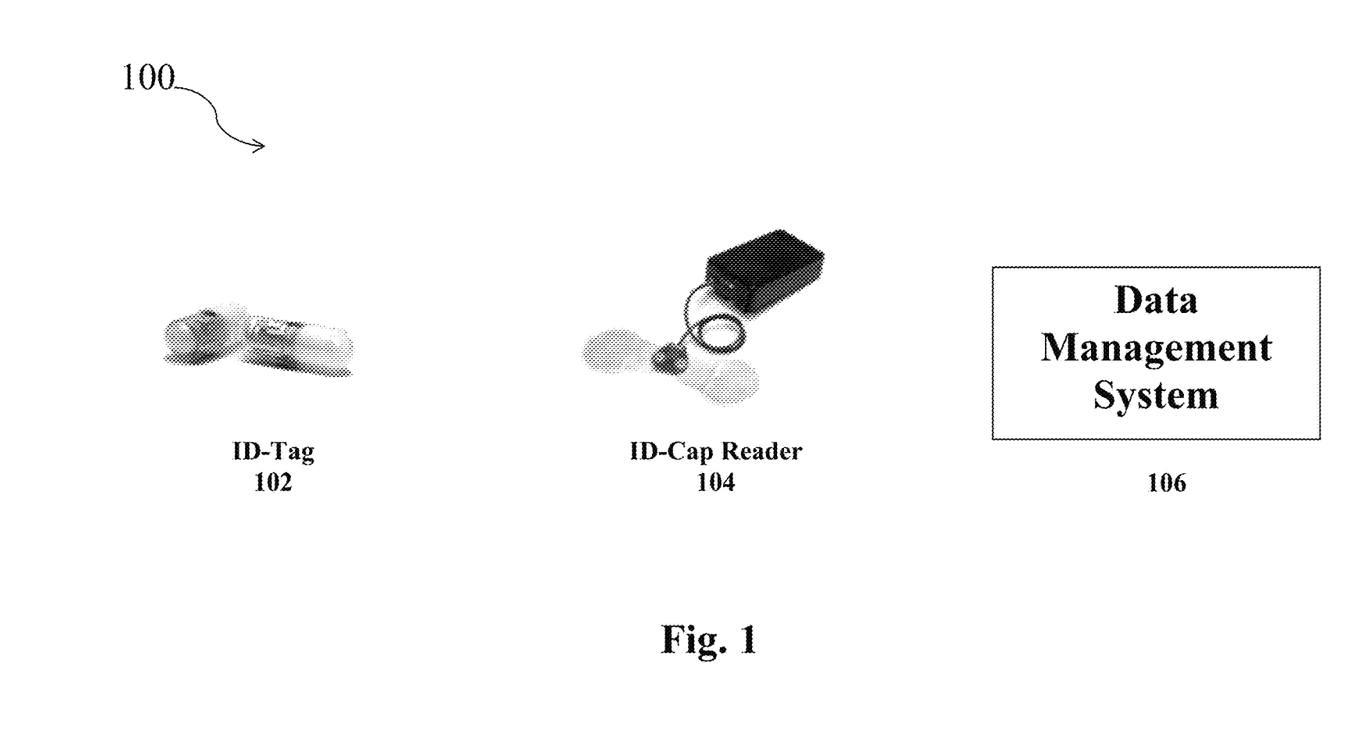
FIG. 1 illustrates an ID-Cap system comprising an ID-Capsule, an ID-Cap Reader, and a remote Data Management System, according to an exemplary aspect.

Twenty (20) healthy volunteers were screened and enrolled in this four-week pilot study. Individuals aged 18 to 45 years who were deemed healthy by the study physician as determined by past medical and surgical history, physical examination, and vital signs at screening were eligible for enrollment in the study. To be eligible, individuals had to weigh at least 50 kg and have a body mass index (BMI) within the range of 18 to 35. Exclusion criteria for the study included the following:

Any known hypersensitivity to silver or magnesium
Difficulty swallowing solids and/or capsules
Any implanted electronic device
A significant illness within two weeks of entering the study
A history of drug or alcohol abuse within the six months prior to screening
Participation in another study at the time of screening or those who have taken an investigational drug within 30 days of enrollment
A significant medical and/or mental condition that would compromise the study participant's welfare or confound the results of this study in the opinion of the investigator
Pregnancy Materials The ID-Cap System may comprise an ingestible sensor system for use in the real-time monitoring and reliable reporting of patient adherence to medication protocols. The ID-Cap System provides an in vivo communications platform that enables verification of the presence of an ingested solid oral dosage form inside the GI tract. Referring to FIG. 1, the ID-Cap System 100 is comprised of three key components:

1) The ID-Tag 102, an ingestible component that sends information from within the body after it has been ingested, 2) The ID-Cap Reader 104, an external receiver that records the data transmitted by the ID-Tag, and 3) An information system 106 configured to monitor ingestion events, manage the data, and send messages to study participants. For example, as shown in FIG. 1, the ID-Tag 102 may be a standard capsule with an embedded ingestible wireless sensor. The ID-Cap Reader 104 may be configured to receive digital messages from the ID-Tag 102 and send them to a central database via a mobile phone network. The data management system 106 may include repository for managing real time ingestion event information and a patient reminder system.

Figure 2:
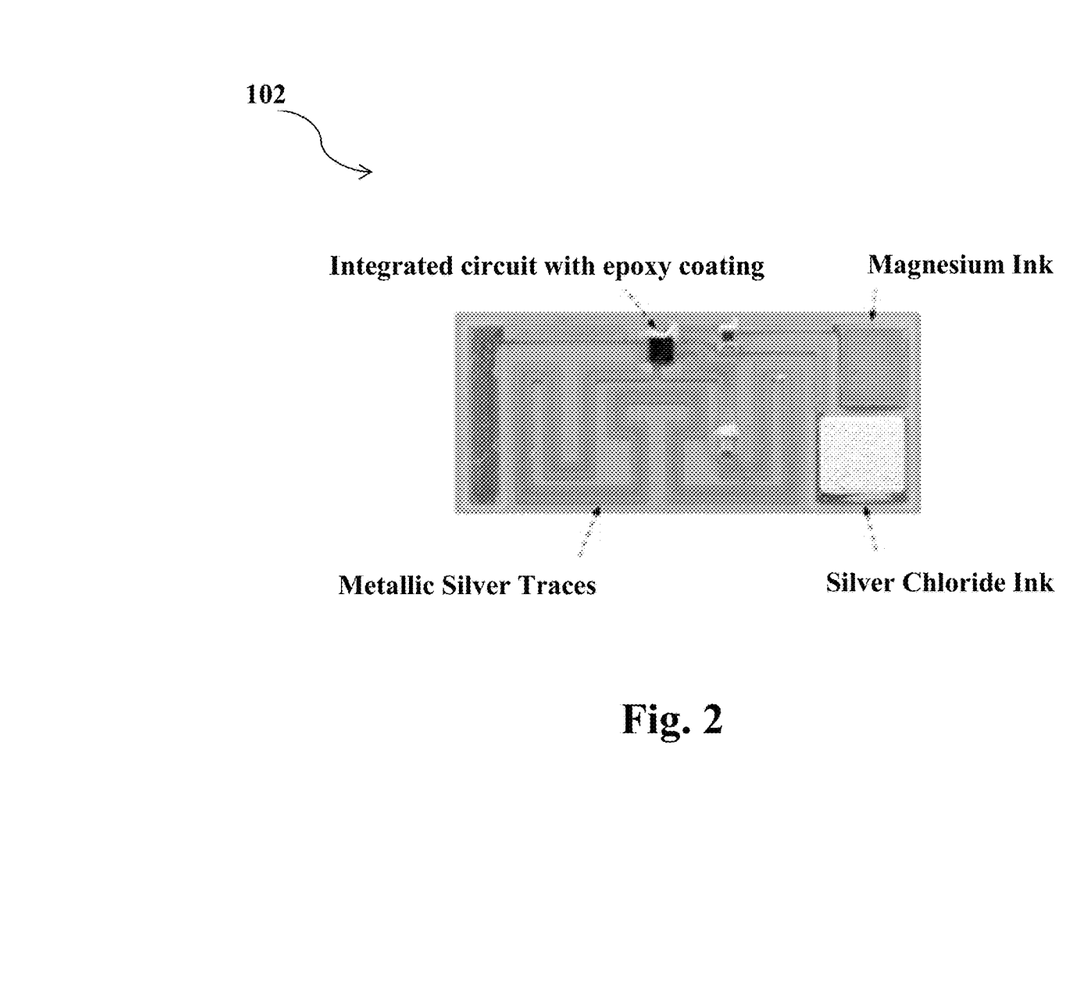
FIG. 2 illustrates the ID-Capsule of the ID-Cap system of FIG. 1, according to an exemplary aspect.

As shown in FIG. 2, the ID-Tag 102 is a small, biocompatible ingestible device that is composed of an integrated circuit on a flexible film (23 mm×10.5 mm×300 microns). The ID-Tag 102 has an exposed sensor that is intended to safely come into contact with the gastrointestinal fluids. The exposed metal elements of the sensor (i.e., magnesium and silver chloride) serve as a battery which powers the ID-Tag 102 to generate the in-body communication signal. Within a few minutes after ingestion of the ID-Tag 102, an electrolyte in the stomach, chloride, powers up the tiny battery on the surface of the ID-Tag 102. This process is independent of the pH of the stomach. The ID-Tag 102 generates a radio frequency signal that propagates through the body and can be detected by the ID-Cap Reader 104, an external receiver. Once ingested and activated, the ID-Tag 102 will transmit the in-body communication signal for approximately 30 minutes on average. After sending the digital messages to the reader 104, the ID-Tag 102 becomes inactive and is excreted intact in the feces. Each ID-Tag 102 can be assigned a distinct identifier, enabling multiple ID-Tags to be detected and differentiated when they are ingested at or around the same time. All materials in the ID-Tag 102 are biocompatible and are either known to be safe or have been safely utilized in other approved ingestible medical devices.

The ID-Tag 102 can be easily incorporated into a capsule for the purpose of providing adherence data for the medication dose that is delivered in the capsule. In this study, the ID-Tag 102 was encapsulated within a size 00 clear hard gelatin capsule that also contained a size 1 hard gelatin capsule filled with sucrose. While the capsules administered in this study represented placebo capsules, the size 00 capsule shell containing the ID-Tag 102 provides a well-characterized and convenient vehicle for delivery of active pharmaceutical ingredients, oral dosage forms, or other ingestible products for which ingestion events will be monitored.

Figure 3:
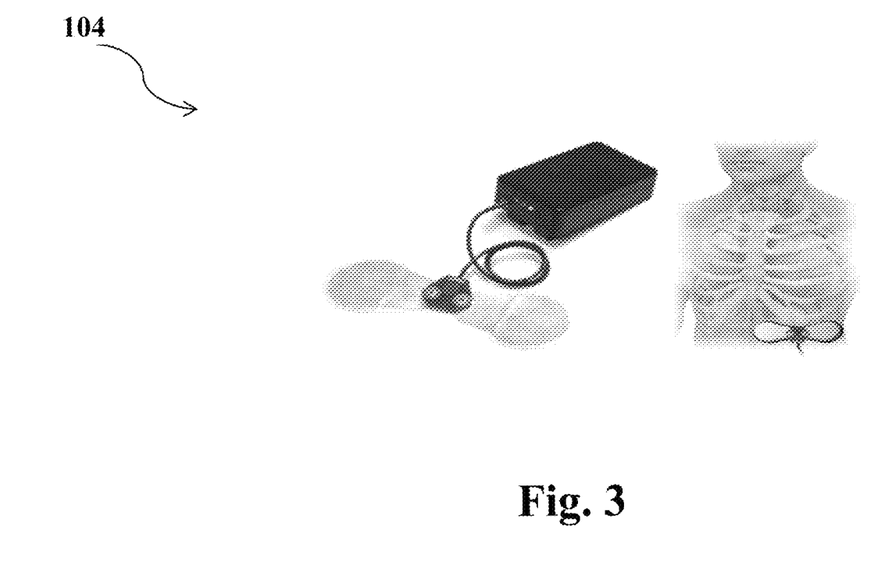
FIG. 3 illustrates the ID-Cap Reader of the ID-Cap system of FIG. 1, according to an exemplary aspect.
Figure 4:
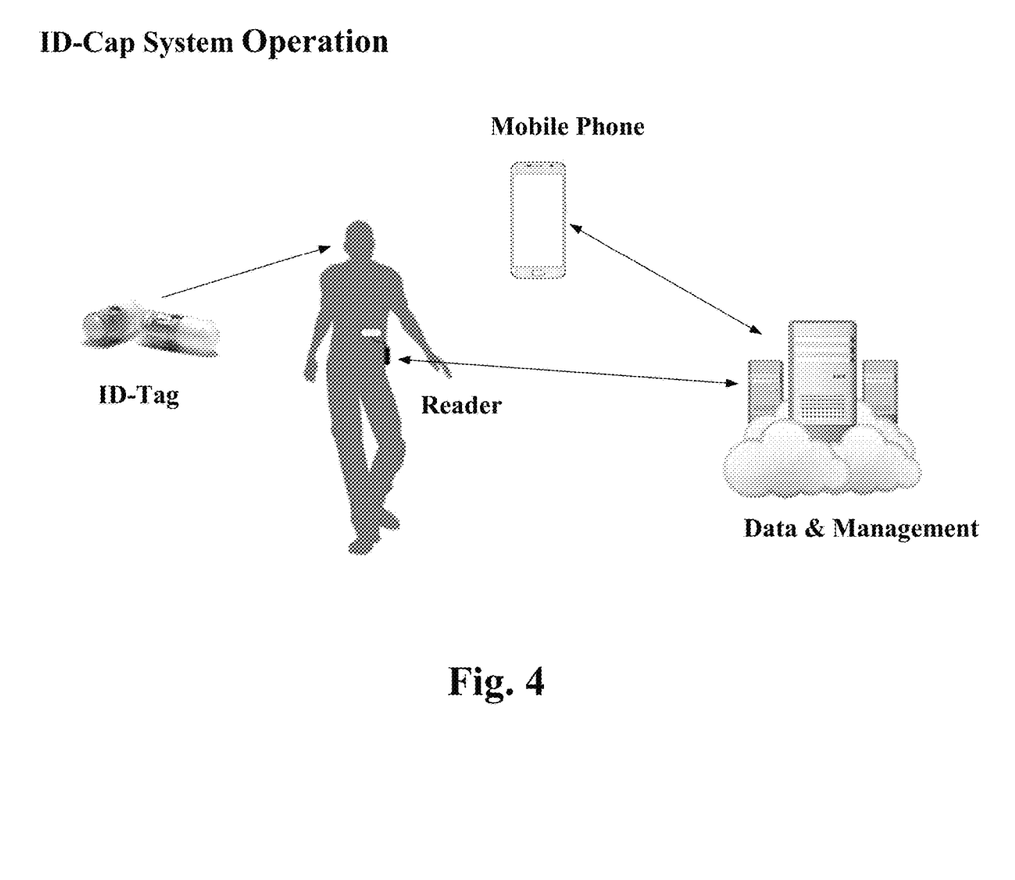
FIG. 4 is a diagram showing system operations among various components of the ID-Cap system of FIG. 1, according to an exemplary aspect.

Referring to FIGS. 3 and 4, the ID-Cap Reader 104 is a wearable, battery-powered, digital radio transceiver that detects the signal generated by the ID-Tag 102 following its ingestion. For example, as shown in FIG. 4, the ID-Tag contains ingestible sensor and medicine that are ingested by a patient and is powered by the patient's stomach fluid. Low-power digital messages and signals are emitted by the ID-Tag from inside the patient for confirming ingestion. The ID-Cap Reader 104 may be configured to detect signal from the ID-Tag and forward data to a secure central database via cell phone system. For this study, the ID-Cap Reader 104 (10 cm×6 cm×2.5 cm) was clipped onto a belt or waistband, and the accompanying patch antenna (16 cm×5.7 cm) was affixed to the skin of the abdomen and connected to the reader with a thin coaxial cable. Study participants were instructed to apply the patch and connect the reader before taking their study capsule and to leave it on for one hour following capsule ingestion. Study participants were also instructed to keep the ID-Cap Reader 104 plugged into an AC power outlet to charge it when they were not wearing the device. A unique ID-Cap Reader 104 was assigned to each study participant.

The wearable reader has three options for uploading data to the software system: cellular, Bluetooth, and USB. The cellular and Bluetooth capabilities allow real-time communication of ingestion events to enable real-time monitoring of medication adherence events and automated, context-sensitive messaging. The stored, encrypted data are securely and privately transmitted from the ID-Cap Reader 104 to the central database. As shown in FIG. 4, the central database may be a cloud data and management system for receiving information of verified, time-stamped, and dose-level adherence events, and may be integrated with data received from other sources (e.g., data from other wearables, devices, and sensors). The central database includes a messaging system to interact with patients (e.g., via a communications portal on mobile phone) and care team and perform various study management and device management functions. The data transmitted by the ID-Cap Reader 104 include the ID-Tag information, unique identifier for the ID-Cap Reader 104, antenna connection status, on-charger status, reader battery status, and device status messages. No personally identifiable information is stored on the ID-Cap Reader 104 or otherwise transmitted throughout the process. The data remain stored on the ID-Cap Reader 104 and can be downloaded directly from the reader as necessary.

Study Design

This open-label, single-arm exploratory study evaluated the performance, reliability, usability, and safety of the ID-Cap System 100 for remote monitoring of 20 ingestion events over four weeks in 20 healthy volunteers. The study endpoints included ID-Tag detection indicating capsule ingestion, utilization of the ID-Cap System 100 consistent with instructions for use, adverse event reports, discontinuations of the System during the study, and safety assessments related to excretion of the ID-Tags through abdominal X-ray evaluations. The study was reviewed and approved by the Western Institutional Review Board (WIRB, Puyallup, Wash.).

The study design included the following three phases: 1) Screening Phase, 2) Treatment Phase consisting of 20 daily capsule ingestion events over a four-week period, and 3) Follow-Up Phase consisting of a follow-up study visit that included an abdominal X-ray and a follow-up phone call.

Screening Phase

Healthy volunteers were screened to determine eligibility for enrollment in the study. Past medical and surgical history, medication history for the prior 30 days, physical examination, body height, body mass index, and vital signs were recorded during the screening visit. After receiving information about the study, each eligible study participant signed the informed consent form. Female participants were given a urine pregnancy test before the treatment phase, at the mid-point of the treatment phase, and before the abdominal X-ray conducted at the follow-up visit. All current medications, as well as their doses and routes of administration, were recorded at the screening visit and at each subsequent study visit.

All study participants were enrolled in a mobile phone message system used to send reminder messages to their personal mobile phones. At a predetermined time each day, the participant received a text message reminding him or her to put on the ID-Cap Reader 104 as directed and to ingest the study capsule if the appropriate ingestion event had not already been recorded. Participants were instructed to call the study staff if any unusual or adverse events were noted between study visits. The study participant also received a follow-up text message one hour after the initial text message if an anticipated ingestion event was not detected with the ID-Cap System 100 within that time window.

Treatment Phase

During the first study visit, participants were reminded of the study plan, provided instructions for taking study capsules, and trained to use the ID-Cap System 100. Study participants were instructed to take one study capsule every day with sufficient water or fluid to comfortably swallow the capsule. They received direction to put on the fully-charged ID-Cap Reader 104 before taking the study capsule and wear it continuously for one hour following capsule ingestion. They were instructed to clip the reader onto a belt or waistband and affix the patch antenna to the skin of the abdomen. They were instructed to replace the patch antenna after each use and to dispose of the used patch antenna. Study participants received instructions on how to charge the reader when not in use. The study capsule consisted of a size 00 hard gelatin capsule that encapsulated both an ID-Tag and a smaller size 1 hard gelatin capsule filled with sucrose.

At the first study visit, the initial use of the ID-Cap Reader 104 and ingestion of the first study capsule were directly observed by the investigator. The investigator recorded the date and time of capsule ingestion, monitored the participant for one hour following ingestion, and reported any adverse events. Subsequent ingestions (i.e., study capsules 2 through 20) were completed outside the research facility at the study participant's home or other location of their choice with ingestion assessed using the ID-Cap System 100. The participant was instructed to record in writing the capsule identification code and the date and time when they took each study capsule on a log that was attached to the back of the ID-Cap Reader 104. The reader 104 was returned to the research facility each week to download the data that were securely stored on it. Study capsules were dispensed to the participant each week. Each study participant received five study capsules to take over the course of a week for four consecutive weeks. Weekly study visits were scheduled with each participant for return of the reader, dispensing of capsules, and collection of any adverse events or usability issues.

Study participants were instructed to call the investigator if they experienced any unusual or adverse events during the treatment phase. If study personnel observed that an assigned device was not functioning as intended or if they were notified of the same, the device was repaired or replaced as needed. If the study participant did not properly recharge the reader prior to its use before taking a study capsule, a replacement capsule was provided for inclusion in the evaluation and the study participant was reminded to use the system as instructed. The data collected from the ID-Cap System 100 included presence of the signal from the ingested ID-Tag 102, other electrical information such as the strength and frequency of the received signal, and information about the status of the reader 104.

Follow-Up Phase

A follow-up study visit conducted at a radiology facility was scheduled within 10 to 14 days after the last study capsule ingestion for assessment of the safety and tolerability of the ID-Cap System 100. This follow-up visit was scheduled with each study participant who ingested at least one study capsule. During the follow-up visit, each study participant met with the investigator for the documentation of any adverse events and received an abdominal X-ray to assess retention of ID-Tags. Female participants were given a urine pregnancy test before the X-ray. Each study participant received a follow-up phone call from the investigator within 30 days after the last study capsule ingestion to assess for any adverse events and to document any changes noted during the study. Changes to medications were also recorded at the follow-up visit and follow-up phone call.

Statistical Analysis Plan

All statistical analyses were descriptive. Summary data for the performance, reliability, and usability of the ID-Cap System 100 included all study participants who ingested at least one study capsule. Summary data for safety and tolerability included all study participants who ingested at least one study capsule.

Results

Twenty-eight (28) individuals were screened to determine eligibility for participation, and 20 healthy volunteers were enrolled in the study. The study population included 12 males and 8 females with a range of ages from 20 to 46 years. Study participants included 15 Caucasian, 3 Hispanic, and 2 African-American individuals with a mean body mass index of 27.8 (range of 20.0 to 34.5). Table 1 provides the demographic information for the 20 enrolled participants.

of 404 study capsules were dispensed to study participants throughout the study, and, thus, 404 ingestion events were remotely monitored using the ID-Cap System 100.

Positive detection accuracy was 100% for the 20 directly-observed ingestions of study capsules that occurred during the initial study visits for all participants. Of the 384 ingestion events that were self-administered by the study participants without direct observation, 371 were accurately detected using the ID-Cap System 100. Overall adherence to the prescribed study capsules as measured by the ID-Cap System 100 was 97.75% (391 detections/400 expected ingestion events) when the reader was used by the study participants according to the instructions for use (excluding the four ingestion events that were not recorded due to operator error for which replacement capsules were tracked). Nine (2.25%) ingestion events were not detected by the system within the one-hour detection window of reader use following self-reported ingestion.

The ID-Cap Readers 104 collected and reliably stored data for all 391 events that were detected using the ID-Cap System 100. Data for 385 of the 391 (98.47%) recorded ingestion events were remotely transmitted from the reader to the secure server in real time. Data for the remaining six ingestion events were downloaded to the server when the

TABLE 1

Study Demographics and Results

| Subject ID | Age (years) | Sex | Race | Height | Weight (pounds) | BMI | Detection of Study Capsule Ingestion | Additional Study Capsule Taken* |
|---|---|---|---|---|---|---|---|---|
| 20-20-001 | 28 | F | Caucasian | 5' | 111 | 21.7 | 20/20 (100%) | 1 |
| 20-20-002 | 24 | F | Caucasian | 5'5" | 167 | 27.8 | 20/20 (100%) | |
| 20-20-003 | 35 | F | Caucasian | 4'11" | 128 | 25.9 | 20/20 (100%) | |
| 20-20-004 | 23 | M | Caucasian | 6'0.5" | 147 | 19.7 | 18/20 (90%) | |
| 20-20-005 | 28 | M | Caucasian | 6'4" | 235 | 28.6 | 19/20 (95%) | |
| 20-20-006 | 29 | M | Caucasian | 6'2" | 214 | 27.5 | 19/20 (95%) | |
| 20-20-007 | 41 | M | Caucasian | 5'9" | 206 | 30.4 | 20/20 (100%) | 1 |
| 20-20-008 | 27 | M | Hispanic | 5'6" | 176 | 28.4 | 20/20 (100%) | |
| 20-20-009 | 20 | M | Hispanic | 6' | 225 | 30.5 | 19/20 (95%) | 1 |
| 20-20-010 | 26 | F | Hispanic | 5'6" | 140 | 22.6 | 19/20 (95%) | |
| 20-20-011 | 30 | F | Caucasian | 5'3" | 189 | 33.5 | 20/20 (100%) | |
| 20-20-012 | 36 | M | African American | 6'6" | 231 | 26.7 | 19/20 (95%) | |
| 20-20-013 | 25 | M | Caucasian | 6'1" | 211 | 27.8 | 20/20 (100%) | |
| 20-20-014 | 25 | M | African American | 5'6" | 178 | 28.7 | 20/20 (100%) | |
| 20-20-015 | 28 | F | Caucasian | 5'5.75" | 212 | 34.5 | 20/20 (100%) | 1 |
| 20-20-018 | 21 | M | Caucasian | 5'11.75" | 239.5 | 32.7 | 20/20 (100%) | |
| 20-20-025 | 30 | F | Caucasian | 5'8.25" | 154 | 23.2 | 20/20 (100%) | |
| 20-20-026 | 31 | M | Caucasian | 6'0.5" | 190 | 25.8 | 20/20 (100%) | |
| 20-20-027 | 46 | F | Caucasian | 5'5" | 154 | 25.6 | 19/20 (95%) | |
| 20-20-028 | 34 | M | Caucasian | 5'10" | 240 | 34.4 h | 20/20 (100%) | |

*Additional study capsule taken due to operator error in fully charging the ID-Cap Reader before use of the ID-Cap System.

Each study participant used the ID-Cap System 100 and took 20 study capsules once daily as directed over a four-week period. No study participants prematurely discontinued use of the ID-Cap System 100 or stopped taking study capsules prior to the end of the treatment period.

Performance, Reliability, and Usability for Ingestion Event Monitoring

A total of 20 study capsules were dispensed to each study participant during the study with instructions to take one capsule once daily. Four study participants were asked to take one additional study capsule as a replacement for an ingestion event that was not recorded due to operator error. In these situations, the study participant did not follow the instructions for recharging the reader prior to its use. A total reader was returned to the research facility by the study participant. Text notifications of successfully-reported ingestion events were automatically sent to each study participant within two to four minutes of the reader detecting a positive signal.

The time that each ingestible sensor was detected in the gastrointestinal tract, indicating when the ID-Tag 102 generated a signal, was also reported using the ID-Cap System 100. Significant intra-individual and inter-individual variability in the timing of self-administered doses was observed in this study.

Safety and Tolerability

No adverse events were reported throughout the study, either through self-reporting by study participants or assessments by study personnel at pre-specified data collection points. No study participants discontinued use of the ID-Cap System 100 for any reason during the study. There was no evidence indicating retention of ID-Tags 102 in any of the 20 study participants based on abdominal X-ray evaluations conducted during follow-up study visits.

This study of the ID-Cap System 100, a novel ingestible sensor system to directly measure medication adherence, provides new information on the performance and potential use of this technology in patient management and clinical trials. The system demonstrated 97.75% accuracy in detecting oral medication use at the level of each dose. In this study, the high level of adherence to self-administered therapy may have been influenced by the daily reminder text messages, weekly study visits allowing reinforcement of medication taking, and, most likely, the well-documented Hawthorne effect. [6] With regard to the latter, the ID-Cap System 100 allows verification and active oversight of medication taking, and study participants were made aware of this functionality and goal of the system through the informed consent process. While the study evaluated the technical feasibility of automated text message reminders as a means for engaging patients related to actual medication use, the study was not designed to modify patient behavior, but rather to report on actual behavior related to medication ingestion. No specific adherence interventions were planned in this study beyond automated reminder text messages and reminder calls from the study investigator, and this presents an area for future study.

For the nine ingestion events that were not detected by the system within the one-hour detection window (9 of 400 events, or 2.25%), either the ID-Tag 102 within the study capsule failed to power up properly or the reader failed to detect the signal generated by the activated ID-Tag 102. The study participants utilized the ID-Cap System 100 over four weeks and a total of 20 doses, demonstrating consistent performance throughout the study and potential applications in monitoring adherence and persistence for chronic medications. The reliability of the verified adherence data generated using this innovative system and valuable information regarding timing of dose ingestion and inter-dose intervals enable meaningful use of this information to transform healthcare and efficiently advance clinical trials. This technology offers unique and valuable insights into actual medication use and objective evidence of adherence, or lack thereof, to strengthen patient treatment plans and clinical research protocols.

This study demonstrated that the ID-Cap System 100 can be successfully used by study participants after simple instruction. User error that impacted system performance occurred in only four instances out of the 404 ingestion events that were monitored throughout this study. Several factors were identified during this study that could contribute to potential failures of the system, including the limited reader battery life, durability of the reader when dropped or exposed to fluids, and design elements that impact patient acceptability and use (e.g., an adhesive patch on the skin). The manufacturer of the ID-Cap System 100 has developed strategies to mitigate the identified risks and has designed a new reader to enhance performance and usability. The system was well tolerated across study participants with no adverse events reported and no discontinuations of the system throughout the 20 days of use. Of note, participants kept the adhesive patch antenna on their abdomen for a limited duration of one hour following capsule ingestion.

Published research involving other ingestible sensor systems have reported significant skin irritation issues with adhesive patches that are used as components of these systems for longer durations. [7] In a preferred embodiment, another version of the ID-Cap System 100 may use external wearable readers that do not require skin contact or adhesive patches, modules that allow integration into widely-used wearable and patient monitoring devices, and other patient-centered form factors, all of which are enabled by the unique in-body communications platform of the ID-Cap System 100.

The ID-Cap System 100 enables accurate measurement of medication adherence for oral drug therapy at the dose level. This study supports the clinical validation of the technology and feasibility in using the system for the collection and real-time reporting of medication adherence in the clinical management of patients and in clinical research and drug development.

REFERENCES

[1] Brown M, Bussell J. Medication adherence: WHO cares? *Mayo Clin Proc* 2011; 86(4):304-314.

[2] Sabaté E, ed. *Adherence to Long-Term Therapies: Evidence for Action*. Geneva, Switzerland: The World Health Organization; 2013.

[3] IMS Institute for Healthcare Informatics. Avoidable costs in U.S. healthcare. 2013. Available at: http://www.imshealth.com/deployedfiles/imshealth/Global/Content/Corporate/IMS%20Institute/RUOM-2013/IHII_Responsible_Use_Medicines_2013.pdf. Accessed Nov. 5, 2015.

[4] Osterberg L, Blaschke T. Adherence to medication. *N Engl J Med* 2005; 353(5):487-497.

[5] Kiourti A, Psathas K, Nikita K. Implantable and ingestible medical devices with wireless telemetry functionalities: a review of current status and challenges. *Bioelectromagnetics* 2014; 35:1-15.

[6] Davis S, Feldman S. Using Hawthorne effects to improve adherence in clinical practice: lessons from clinical trials. *JAMA Dermatol* 2013; 149(4):490-491.

[7] Eisenberger U, Wüthrich R, Bock A, et al. Medication adherence assessment: high accuracy of the new ingestible sensor system in kidney transplants. *Transplantation* 2013; 96:245-250.

What is claimed is:

1. A system for ingestion event monitoring, the system comprising:
   a plurality of ingestible microsensors ingested by a patient around the same time, each ingestible microsensor being configured to generate a signal indicating an ingestion event upon ingestion and contact with stomach fluid, each ingestible microsensor being associated with a unique identifier, and the signal generated by each ingestible microsensor comprising data indicating the unique identifier; and
   a reader device positioned external to the patient and configured to detect and differentiate the signal transmitted from each of the plurality of ingestible microsensors with at least 95% accuracy based at least on the unique identifier associated with each ingestible microsensor.

2. The system of claim 1, further comprising a remote database configured to receive data from the reader device via a communication network in real time, and generate and transmit one or more messages at least to the patient based upon received data from the reader device.

3. The system of claim 2, wherein the data comprise information relating to each ingestible microsensor, a unique identifier of the reader device, antenna connection status, charging information of the reader device, reader device battery status, and device status messages.

4. The system of claim 2, wherein the one or more messages comprise automated text messages and reminders to improve a patient's medication adherence.

5. A system for ingestion event monitoring, the system comprising:
- a plurality of ingestible microsensors ingested by a plurality of patients over a period of time, each ingestible microsensor being configured to generate a signal indicating an ingestion event upon ingestion and contact with stomach fluid, each ingestible microsensor being associated with a unique identifier, and the signal generated by each ingestible microsensor comprising data indicating the unique identifier;
- a reader device assigned to each patient, positioned external to each patient following ingestion, and configured to detect the signal transmitted from each of the plurality of ingestible microsensors with at least 95% accuracy; and
- a remote database configured to receive data from the reader device via a communication network in real time, and generate and transmit one or more messages at least to each patient based upon received data from the reader device,
- wherein the data comprise information relating to each ingestible microsensor, a unique identifier of the reader device, antenna connection status, charging information of the reader device, reader device battery status, and device status messages.

6. The system of claim 5, wherein the one or more messages comprise automated text messages and reminders to improve a patient's medication adherence.

7. The system of claim 1, wherein the reader device requires no skin contact with the patient.

8. A method for ingestion event monitoring, the method comprising:
- embedding each of a plurality of ingestible microsensors in an oral dosage form to be consumed by a subject; and
- having the subject ingest the oral dosage form of each of the plurality of ingestible microsensors;
- wherein each ingestible microsensor is configured to generate a signal indicating an ingestion event upon contact with stomach fluid of the subject, and transmit the signal to a reader device positioned external to the subject, wherein each ingestible microsensor is associated with a unique identifier, and the signal generated by each ingestible microsensor comprises data indicating the unique identifier, wherein the reader device is configured to detect and differentiate the signal transmitted from each ingestible microsensor with at least 95% accuracy based at least on the unique identifier associated with each ingestible microsensor.

9. The method of claim 8, wherein each ingestible microsensor comprises circuitry configured to generate power upon being exposed to the stomach fluid of the subject, and each ingestible microsensor is configured to generate and transmit the signal using the power over a period of time following ingestion.

* * * * *